US00PP31797P2

(12) United States Plant Patent
Lannes

(10) Patent No.: US PP31,797 P2
(45) Date of Patent: May 26, 2020

(54) ***MANDEVILLA* PLANT NAMED 'LANMASSACHUSETTS'**

(50) Latin Name: *Mandevilla hybrida*
Varietal Denomination: Lanmassachusetts

(71) Applicant: Robert Lannes, Malause (FR)

(72) Inventor: Robert Lannes, Malause (FR)

(73) Assignee: D.H.M. Innovation S.A.S., Malause (FR)

( * ) Notice: Subject to any disclaimer, the term of this patent is extended or adjusted under 35 U.S.C. 154(b) by 0 days.

(21) Appl. No.: 16/350,757

(22) Filed: Dec. 31, 2018

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./232, 226

CPC ... A01H 5/02; A01H 5/00; A01H 5/12; A01H 6/088; A01H 6/08
See application file for complete search history.

(56) References Cited

PUBLICATIONS

Floral Daily 2018 Preview FlowerTrials #3, retrieved on Sep. 9, 2017, retrieved from the Internet at https://www.floraldaily.com/article/9015612/preview-flowertrials-3/, 12 pp. (Year: 2018).*

* cited by examiner

*Primary Examiner* — June Hwu
(74) *Attorney, Agent, or Firm* — C. A. Whealy

(57) ABSTRACT

A new and distinct cultivar of *Mandevilla* plant named 'Lanmassachusetts', characterized by its compact and upright plant habit; low vigor to moderately vigorous growth habit; relatively thick leaves and petals; glossy dark green-colored leaves; freely flowering habit; and large light red purple-colored flowers with a darker red purple and orange-colored center "star".

2 Drawing Sheets

Botanical designation: *Mandevilla hybrida.*
Cultivar denomination: 'LANMASSACHUSETTS'.

BACKGROUND OF THE INVENTION

The present invention relates to a new and distinct cultivar of *Mandevilla* plant, botanically known as *Mandevilla hybrida* and hereinafter referred to by the name 'Lanmassachusetts'.

The new *Mandevilla* plant is a product of a planned breeding program conducted by the Inventor in Malause, France. The objective of the breeding program is to create new compact *Mandevilla* plants with large attractive flowers.

The new *Mandevilla* plant originated from a cross-pollination conducted by the Inventor in Malause, France in July, 2012 of *Mandevilla hybrida* 'Lannorthcarolina', disclosed in U.S. Plant Pat. No. 25,851, as the female, or seed, parent with *Mandevilla hybrida* 'Lanalabama', not patented, as the male, or pollen, parent. The new *Mandevilla* plant was discovered and selected by the Inventor as a single flowering plant from within the progeny of the stated cross-pollination in a controlled greenhouse environment in Malause, France in July, 2016.

Asexual reproduction of the new *Mandevilla* plant by vegetative stem cuttings in a controlled environment in Malause, France, since July, 2017 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following trails have been repeatedly observed and are determined to be the unique characteristics of 'Lanmassachusetts'. These characteristics in combination distinguish 'Lanmassachusetts' as a new and distinct *Mandevilla* plant:

1. Compact and upright plant habit.
2. Low vigor to moderately vigorous growth habit.
3. Relatively thick leaves and petals.
4. Glossy dark green-colored leaves.
5. Freely flowering habit.
6. Large light red purple-colored flowers with a darker red purple and orange-colored center "star".

Plants of the new *Mandevilla* can be compared to plants of the female parent, 'Lannorthcarolina'. Plants of the new *Mandevilla* differ primarily from plants of 'Lannorthcarolina' in the following characteristics:

1. Plants of the new *Mandevilla* have shorter internodes than plants of 'Lannorthcarolina'.
2. Leaves of plants of the new *Mandevilla* are thicker and smoother than leaves of plants of 'Lannorthcarolina'.
3. Plants of the new *Mandevilla* have larger flowers than plants of 'Lannorthcarolina'.
4. Petals of plants of the new *Mandevilla* are thicker than petals of plants of 'Lannorthcarolina'.

Plants of the new *Mandevilla* can be compared to plants of the male parent, 'Lanalabama'. Plants of the new *Mandevilla* differ primarily from plants of 'Lanalabama' in the following characteristics:

1. Plants of the new *Mandevilla* are not as vigorous or as vining as plants of 'Lanalabama'.
2. Plants of the new *Mandevilla* have light red purple-colored flowers with a darker red purple and orange-colored center "star" whereas plants of 'Lanalabama' have red-colored flowers.

Plants of the new *Mandevilla* can also be compared to plants of *Mandevilla hybrida* 'Lansouthcarolina', disclosed in U.S. Plant Pat. No. 26,406. In side-by-side comparisons, plants of the new *Mandevilla* differ primarily from plants 'Lansouthcarolina' in the following characteristics:

1. Plants of the new *Mandevilla* have shorter internodes than plants of 'Lansouthcarolina'.
2. Leaves of plants of the new *Mandevilla* are thicker and smoother than leaves of plants of 'Lansouthcarolina'.
3. Plants of the new *Mandevilla* have larger flowers than plants of 'Lansouthcarolina'.
4. Petals of plants of the new *Mandevilla* are thicker than petals of plants of 'Lansouthcarolina'.
5. Plants of the new *Mandevilla* have light red purple-colored flowers with a darker red purple and orange-colored center "star" whereas plants of 'Lansouthcarolina' have pink-colored flowers.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'Lanmassachusetts' grown in a container.

The photograph on the second sheet is a close-up view of a typical open flower of 'Lanmassachusetts'.

DETAILED BOTANICAL DESCRIPTION

The aforementioned photographs and following observations, measurements and values describe plants grown during the winter with three plants in a 21-cm containers in a polyethylene-covered greenhouse in Malause, France and under cultural practices typical of commercial *Mandevilla* production. During the production of the plants, day temperatures ranged from 18° C. to 23° C. and night temperatures ranged from 15° C. to 18° C. Plants were seven months old when the photographs and description were taken. In the following description, color references are made to The Royal Horticultural Society Colour Chart, 2015 Edition, except where general terms of ordinary dictionary significance are used.

Botanical classification: *Mandevilla hybrida* 'Lanmassachusetts'.

Parentage:

*Female, or seed, parent.*—*Mandevilla hybrida* 'Lannorthcarolina', disclosed in U.S. Plant Pat. No. 25,851.

*Male, or pollen, parent.*—*Mandevilla hybrida* 'Lanalabama', not patented.

Propagation:

*Type.*—By vegetative cuttings.

*Time to initiate roots, summer.*—About two weeks at temperatures about 23° C. to 30° C.

*Time to initiate roots, winter.*—About three weeks at temperatures about 23° C. to 25° C.

*Time to produce a rooted young plant, summer.*—About five to six weeks at temperatures about 23° C. to 30° C.

*Time to produce a rooted young plant, winter.*—About six to eight weeks at temperatures about 23° C. to 25° C.

*Root description.*—Fine, fibrous; typically light yellowish white in color, actual color of the roots is dependent on substrate composition, water quality, fertilizers, substrate temperature and physiological age of roots.

*Rooting habit.*—Freely branching; medium density.

Plant description:

*Plant and growth habit.*—Compact and upright plant habit; overall plant shape is broadly oblong; low vigor to moderately vigorous growth habit and low to moderate growth rate.

*Plant height, soil level to top of foliar plane.*—About 23.7 cm.

*Plant height, soil level to top of floral plane.*—About 25.7 cm.

*Plant diameter (spread).*—About 25.3 cm.

*Lateral branch description.*—Branching habit: Freely branching habit, primary lateral branches with typically two secondary lateral branches developing per plant. Length: About 8.8 cm. Diameter: About 4 mm. Internode length: About 4 cm. Aspect: Primary lateral branches, about 10° from vertical; secondary lateral branches, about 20° from primary branch axis. Strength: Strong. Texture and luster: Smooth, glabrous; glossy; becoming woody with development. Color, developing: Close to 144B. Color, developed: Close to 144B; when woody, close to 199C.

Leaf description:

*Arrangement.*—Opposite, simple.

*Length.*—About 14.2 cm.

*Width.*—About 8.2 cm.

*Shape.*—Elliptic to oblong.

*Apex.*—Short apiculate.

*Base.*—Truncate.

*Margin.*—Entire.

*Texture and luster, upper surface.*—Smooth, glabrous; moderately coriaceous; glossy.

*Texture and luster, lower surface.*—Smooth, glabrous; moderately coriaceous; moderately glossy.

*Venation pattern.*—Pinnate.

*Color.*—Developing leaves, upper surface: Close to between 144A and 146A. Developing leaves, lower surface: Close to between 143A and 144A. Full expanded leaves, upper surface: Darker than between NN137A and 147A; venation, close to 143A to 143B. Fully expanded leaves, lower surface: Close to 146B; venation, close to 144B.

*Petioles.*—Length: About 1.2 cm. Diameter: About 3.5 mm by 4 mm. Strength: Moderately strong. Texture and luster, upper and lower surfaces: Smooth, glabrous; moderately glossy. Color, upper surface: Close to 144A. Color, lower surface: Close to 144B.

Flower description:

*Flower type and flowering habit.*—Single salverform flowers arranged singly or in axillary cymes; flowers star-shaped, moderately asymmetric and face mostly outwardly to slightly upright; freely flowering habit with about two flowers developing per inflorescence and about 74 flower buds and flowers develop per plant.

*Natural flowering season*.—Plants flower continuously from spring into the autumn in France; plants begin flowering about 20 weeks after planting.

*Flower longevity on the plant*.—About 15 days; flowers not persistent.

*Fragrance*.—None detected.

*Inflorescence height*.—About 9 cm.

*Inflorescence diameter*.—About 10.6 cm.

*Flower buds*.—Length: About 6.2 cm. Diameter: About 1 cm. Shape: Narrowly oblanceolate. Texture and luster: Smooth, glabrous; slightly glossy. Color: Close to 39B; towards the base, close to 145B to 145C; tube, close to 144C.

*Flowers*.—Appearance: Flared trumpet, corolla fused and five-parted. Diameter: Large, about 11 cm. Depth (length): About 7 cm. Throat diameter: About 1.5 cm. Tube length: About 4.1 cm. Tube diameter: Distally, about 1.5 cm; proximally, about 6 mm.

*Petals*.—Quantity and arrangement: Five petals arranged in a single whorl; lower 40% portion of the petals are fused into a funnelform tube. Petal length: About 9.2 cm. Petal width: About 4.1 cm. Petal shape and appearance: Roughly spatulate. Petal apex: Apiculate. Petal margin: Entire; moderately undulate. Petal texture and luster, upper surface: Smooth, glabrous; moderately velvety; matte. Petal texture and luster, lower surface: Smooth, glabrous; slightly velvety; matte. Throat texture: Smooth, glabrous; moderately velvety. Tube texture: Smooth, glabrous; slightly velvety. Color: Petal, when opening, upper surface: Close to 65C to 65D; fading towards the throat to close to 150D and 155A. Petal, when opening, lower surface: Close to 145D; towards the margins, close to 51C and 69D. Petal, fully opened, upper surface: Close to 62B and 65A; fading towards the throat to close to N155B; center "star", close to 58B to 58C tinged with close to 28B; venation, similar to lamina color; color does not change with development. Petal, fully opened, lower surface: Close to 65C; broad margins, close to 58D; main vein, close to NN155C; color does not change with development. Throat: Close to 9A; proximally, close to 144B; venation, similar to lamina. Tube: Close to 144A; distally, close to 144B and 144C; venation, similar to lamina.

*Sepals*.—Quantity and arrangement: Five sepals arranged in a single whorl. Calyx length: About 8 mm. Calyx diameter: About 1.1 cm. Sepal length: About 8 mm. Sepal width: About 2 mm. Sepal shape: Narrowly deltoid to lanceolate. Sepal apex: Narrowly acute. Sepal base: Broadly cuneate. Sepal margin: Entire. Sepal texture and luster, upper surface: Smooth, glabrous; moderately glossy. Sepal texture and luster, lower surface: Smooth, glabrous; slightly glossy. Sepal color: When opening, upper and lower surfaces: Close to 144C; towards the margins and apex, close to 180A to 180B. Fully opened, upper and lower surfaces: Close to 144B; towards the margins and apex, close to 180B.

*Peduncles*.—Length: About 9.2 cm. Diameter: About 3 mm. Strength: Strong. Aspect: About 20° from vertical. Texture and luster: Smooth, glabrous; glossy. Color: Close to 144A to 144B.

*Pedicels*.—Length: About 1.2 cm. Diameter: About 3 mm. Strength: Strong. Aspect: About 25° from peduncle axis. Texture and luster: Smooth, glabrous; moderately glossy. Color: Close to 144A.

*Reproductive organs*.—Stamens: Quantity and arrangement: Typically five; basifixed; anthers connivent. Filament length: About 1.5 mm. Filament color: Close to 151D. Anther size: About 7 mm by 1.5 mm. Anther shape: Narrowly oblong. Anther color: Close to 160C. Pollen amount: None observed. Pistils: Quantity: Typically one. Pistil length: About 1.5 cm. Style length: About 1.3 cm. Style color: Close to 145C to 145D. Stigma diameter: About 2.5 mm. Stigma shape: Club-shaped, pointed. Stigma color: Close to 144A. Ovary color: Close to 143B.

*Seeds and fruits*.—To date, seed and fruit production have not been observed on plants of the new *Mandevilla*.

Pathogen & pest resistance: To date, plants of the new *Mandevilla* have not been noted to be resistant to pathogens and pests common to *Mandevilla* plants.

Temperature tolerance: Plants of the new *Mandevilla* have been observed to tolerate high temperatures of about 40° C. and to be suitable for USDA Hardiness Zones 9 through 13.

It is claimed:

1. A new and distinct *Mandevilla* plant named 'Lanmassachusetts' as illustrated and described.

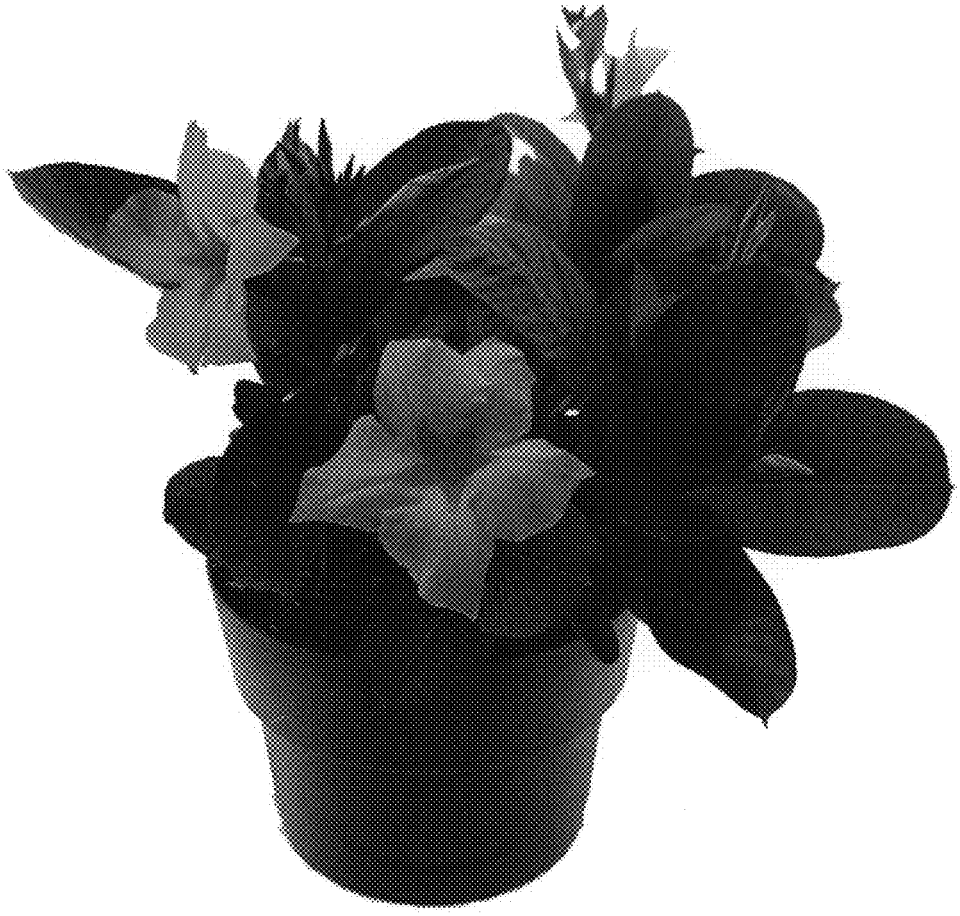

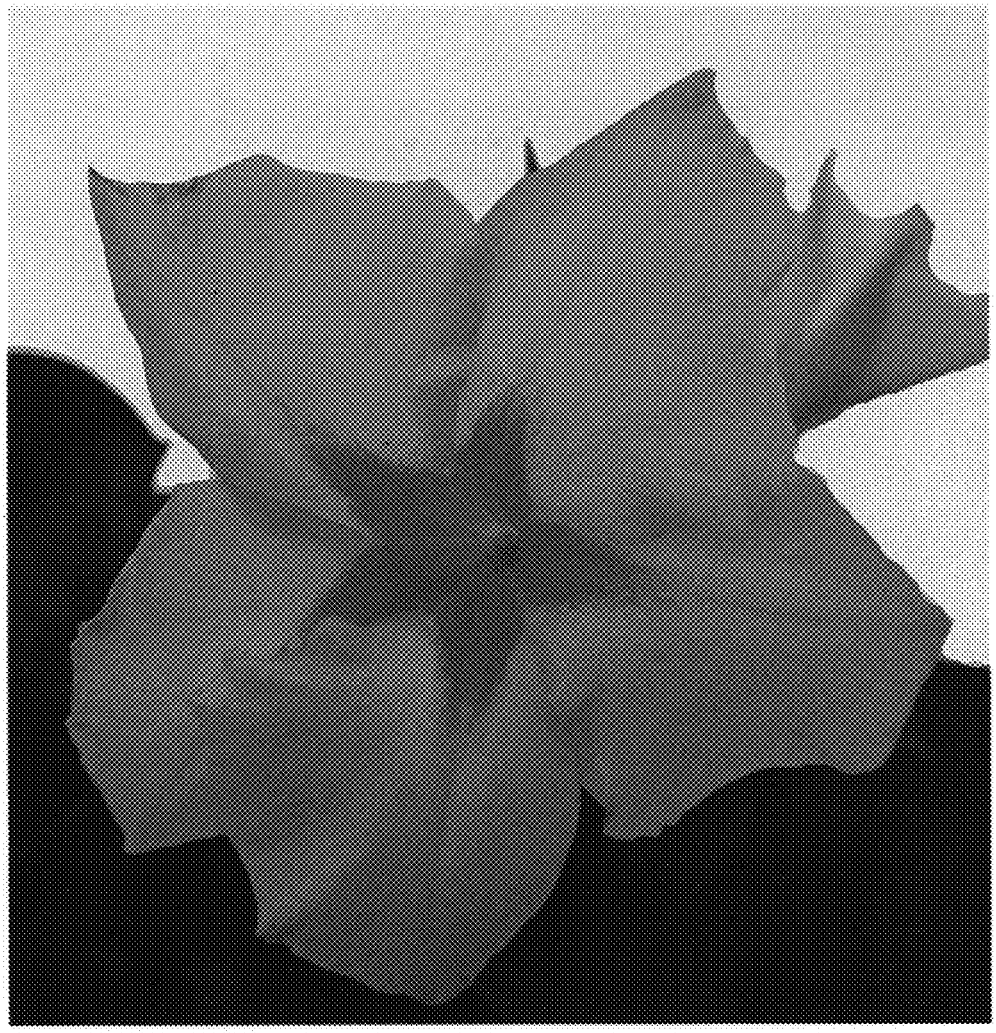

* * * * *